United States Patent [19]
Lee et al.

[11] Patent Number: 6,146,377
[45] Date of Patent: Nov. 14, 2000

[54] BREAST STABILIZATION DEVICES AND METHODS

[75] Inventors: Roberta Lee, Redwood City; James W. Vetter, Portola Valley; Natalie N. Hyland, Redwood City, all of Calif.

[73] Assignee: Rubicor Medical, Inc., Redwood City, Calif.

[21] Appl. No.: 09/158,215

[22] Filed: Sep. 22, 1998

[51] Int. Cl.[7] .................................................. A61B 5/055
[52] U.S. Cl. .......................................... 606/13; 600/414
[58] Field of Search ......................... 606/1, 130; 600/38, 600/411, 414

[56] References Cited

U.S. PATENT DOCUMENTS

| | | |
|---|---|---|
| 4,130,112 | 12/1978 | Frazer . |
| 4,347,850 | 9/1982 | Kelly-Fry et al. . |
| 4,563,768 | 1/1986 | Read et al. . |
| 4,691,333 | 9/1987 | Gabriele et al. . |
| 5,009,660 | 4/1991 | Clapham . |
| 5,171,321 | 12/1992 | Davis . |
| 5,308,321 | 5/1994 | Castro . |
| 5,437,280 | 8/1995 | Hussman . |
| 5,702,405 | 12/1997 | Heywang-Koebrunner . |
| 5,810,742 | 9/1998 | Pearlman . |

FOREIGN PATENT DOCUMENTS

| | | |
|---|---|---|
| 40 37 387 | 5/1992 | Germany . |
| 1 214 707 | 12/1970 | United Kingdom . |
| 95 21582 | 8/1995 | WIPO . |
| WO 99/08647 | 2/1999 | WIPO . |

Primary Examiner—Michael Buiz
Assistant Examiner—William W. Lewis
Attorney, Agent, or Firm—Young Law Firm, P.C.

[57] ABSTRACT

A breast stabilization device includes a substantially rigid outer member and an inner member joined to the outer member. The inner member is configured to conform to the shape of the female breast. An opening is disposed through the outer and inner members, the opening being centered on the nipple/areolar complex of the breast and exposing at least a portion of the areola surrounding the nipple. A rigid rim may surround the periphery of the opening and may rise above the surface of the outer member. The device stabilizes the breast in an uncompressed or slightly expanded state to allow interventional and imaging procedures to be carried out without compressing the breast. The opening allows access to the breast through the areola and the rim allows one or more instruments to be attached thereto. A method of imaging a breast, according to the present invention, includes the steps of placing a generally breast shaped member on the breast, the breast shaped member having one or more imaging port therein; expanding the breast to come into intimate contact with the breast shaped member; and imaging the breast through the imaging port(s). The imaging step may be carried out by directing ultrasonic energy through the port(s).

34 Claims, 1 Drawing Sheet

BREAST STABILIZATION DEVICES AND METHODS

BACKGROUND OF THE INVENTION

1. Field of the Invention

The present invention pertains to the field of diagnostic and therapeutic medical devices and procedures. More particularly, the present invention relates to the field of stabilization, imaging and procedure facilitating platforms for the female breast.

2. Description of the Related Art

Conventional breast stabilization devices and methods are a direct consequence from the technique of mammography. To obtain an acceptable mammographic image, the breast must be compressed and held immobile between two parallel plates. With the use of mammography to localize lesions for diagnostic procedures, the breast had to remain between the two compression plates for imaging and thereafter, to provide a platform from which to conduct the diagnostic procedure.

Compression of the breast is mandatory for a stereotactic biopsy. Indeed, compression is required to obtain the required mammographic views, as an adequate mammogram cannot be obtained unless the breast is in compression. The computer calculates the x, y and z coordinates targeting the lesion. The breast stays in compression during the entire localization and biopsying procedure.

Because of the required compression, the placement of the compression plates on the woman's breast determines the skin entry site for the procedure and, therefore, the scar location. Indeed, the position of the breast in the compression device dictates where the incision is to be made. The scar is most always on the side of the breast, whether superior, lateral, inferior or medial. The scar can range from about 5 mm in length to an unsightly 3 cm if a large coring device is used.

Examples of such devices and methods include that disclosed in U.S. Pat. No. 5,702,405 issued Dec. 30, 1997 to Heywang-Koebrunner. As described in this reference, the breast is compressed between two plates of a stereotactic attachment to a tomography device. Through holes are disposed in one of the two compression plates at an oblique angle within a plane that is substantially perpendicular to the plane of the plates, to allow a biopsy needle to access the breast through the side thereof Similarly, U.S. Pat. No. 4,563,768 to Read et al. discloses a mammographic device utilizing two parallel plates to compress the breast. One of the compression plates functions as an X-ray film holder. A matrix of perforations is disposed in one the compression plates, allowing access to the side of the breast by a biopsy needle or the like. U.S. Pat. No. 4,691,333 uses similar breast compression and side access technology. LaBash, in U.S. Pat. No. 5,499,989 discloses yet another breast compression scheme, in which the breast is stabilized by compression, whereupon a guide spool is aligned over an opening in one of the plates. The guide spool guides a tubular punch or a biopsy needle through the breast to the lesion site, puncturing the side of the compressed breast.

These and other similar devices share a number of disadvantages. From the patient's perspective, such breast compression devices and associated procedures are uncomfortable, awkward and painful. Indeed, such techniques often require the patient to assume an uncomfortable position to fit one of her breasts between the plates, which are then moved toward one another to compress the breast therebetween. This can be quite painful, as the degree of compression necessary to properly stabilize the breast in this manner is quite great.

To complicate matters, breast tissue often does not compress evenly, as the breast tissue may have localized regions of relatively greater or lesser densities that may slide against one another, a denser region being likely to push a relatively less dense area out of the way as the breast is compressed between the two parallel plates. In addition, the breast may have been slightly twisted as it was compressed. After an invasive procedure during which the breast was compressed as described above, the breast tissue expands, and the apparent profile of the path followed by the needle or other device (often coring its way through the tissue) may no longer be the straight path taken by the device when the breast was compressed. This results in an often curved or somewhat tortuous cavity in the breast. With a large coring device, this can cause permanent distortion and disfigurement.

Scars along the border of the areola are much less noticeable than scars of similar length made in the side surface of the breast. The areola is an ideal point of entry into the breast, as compared with the side top or bottom of the breast. However, conventional breast stabilizing devices are designed to allow access to the interior of the breast only from the side of the breast and not from the areola border.

Another technique for sampling or excising lesions in the breast involves sonographically targeting the lesion and manually carrying out a fine needle aspiration, core biopsy or vacuum assisted core biopsy. In such a procedure, the breast is not compressed and an ultrasound transducer is typically used to image the breast and the site of interest therein. In ultrasound guided biopsy, the physician must manually stabilize the breast, hold the ultrasound probe, and perform the biopsy accurately enough to obtain tissue from the lesion. Conventionally, this procedure is carried out by inserting the needle within the breast in an orientation that is as near parallel to the patient's chest wall as possible. The breast stabilization, the operation of the probe, as well as the actual needle biopsy must be carried out simultaneously, all the while maintaining the needle within the focal plane of the ultrasound probe. It is difficult to have an assistant help perform the procedure because if the ultrasound probe and/or needle are not exactly in line and are off by a fraction of a millimeter, then the needle cannot be visualized on the ultrasound monitor. Moreover, any movement of the patient (e.g., coughing, shifting) will also cause the biopsy device and ultrasound probe to misalign.

Imaging and invasive procedures on the uncompressed breast will alleviate the disadvantages associated with compressing the breast. Importantly, such procedures on the uncompressed breast would be less painful, would allow more choices for the entry site and would provide a means for excising tissue from the breast in its natural state.

SUMMARY OF THE INVENTION

It is, therefore, an object of the present invention to provide a device and a method for stabilizing the breast that is more comfortable and less painful than conventional devices. Another object of the present invention is a breast stabilization device and method that effectively immobilizes the breast without resorting to compression and that does not share the disadvantages associated with compressing the breast. A further object is to provide a procedure facilitating platform that allows imaging and invasive procedures to be performed on the uncompressed breast. It is a further object of the present invention to provide a platform that overcomes the disadvantages of previous devices, such as 1) inability to pick entry site; 2) distortion of the breast caused by compression and 3) inability to accurately assess margins in a compressed breast.

In accordance with the above-described objects and those that will be mentioned and will become apparent below, an embodiment of a breast stabilizing device for imaging and invasive procedures according to the present invention comprises:

a substantially rigid outer member;

an inner member joined to the outer member, the inner member being configured to generally conform to a shape of a female breast; and an opening disposed through the outer and inner members, the opening being aligned with a nipple/areola complex of the breast.

According to further embodiments, a rigid rim may be provided, the rigid rim surrounding a periphery of the opening and rising above a surface of the outer member. The rigid rim may include a lip configured to allow at least one instrument to be secured thereto. The rim may be integral to the outer member or may be separate and detachable therefrom.

The opening may be configured to expose at least a portion of an areola surrounding the nipple. The inner member may comprise a curved base portion configured to support the device against a patient's chest. A first sealing edge may be provided around the opening, the first sealing edge being configured to seal the breast to the opening. The first sealing edge may include a first adhesive layer disposed thereon. The base portion may comprise a second sealing edge, the second sealing edge being configured to seal the device to the patient's chest. The second sealing edge may include a second adhesive layer disposed thereon. One or more imaging ports may be disposed within a side surface of at least the outer member. An imaging port rim adapted to fit within the imaging port may also be provided, the imaging port rim allowing at least one imaging instrument to be secured thereto. An imaging port sealing edge surrounding each of the at least one imaging port may be provided, each imaging port sealing edge being configured to seal the breast around its corresponding imaging port. The inner member may include an inner member adhesive layer disposed on a surface thereof facing the breast. The inner member may include a plurality of through holes disposed therein. The inner member and the outer member may be configured to form a substantially gas-tight interstitial space therebetween and the device further may comprise at least one suction port disposed in the outer member. Securing means may be attached to the outer member, the securing means securing the breast stabilization device to at least one of a table and a chair. The securing means may include a substantially rigid band girdling the breast stabilizing device. The inner member may be relatively more flexible than the outer member.

The present invention may also be viewed as a method of stabilizing an uncompressed breast, comprising the steps of:

placing a generally breast-shaped member over the uncompressed breast, the breast-shaped member including an opening aligned with and exposing at least a portion of a nipple/areolar complex of the breast; and sealing the breast within the shaped-shaped member by means of at least one of an adhesive and a vacuum-induced force that draws the breast thereto. A step of securing the cup-shaped member to a stable positional reference structure may also be carried out.

According to another embodiment, a procedure facilitating platform for a breast, according to the present invention comprises:

a generally breast shaped member configured to cover at least a portion of the breast;

suction means for drawing the breast shaped member in close contact with the breast; and a first access port disposed in the generally breast shaped member.

According to still further embodiments, the first access port may be centered on the nipple/areolar complex of the breast. One or more second access ports maybe provided, the second access port(s) being disposed in a side of the generally breast shaped member.

The present invention, according to a still further embodiment, is a method of imaging a breast, comprising the steps of:

placing a generally breast shaped member on the breast, the breast shaped member having a first imaging port therein;

expanding the breast to come into intimate contact with the breast shaped member; and imaging the breast through the first imaging port.

The expanding step may be carried out by creating a partial vacuum between the breast and the breast shaped member. The first imaging port may expose a portion of the breast therethrough and the imaging step may include a step of directing ultrasonic energy into the breast through the first imaging port. A step of applying an ultrasound coupling medium within the first imaging port prior to the directing step may also be carried out. The breast shaped member may also include a second imaging port and the imaging step may image the breast through the first and the second imaging ports. The breast may be imaged through the first and second imaging ports simultaneously. The imaging step may generate imaging data and the imaging data may be transmitted to at least one data processing and display device. The method may also comprise the steps of processing imaging data obtained from each of the first and second imaging ports in a data processing and display device; and displaying the processed image data as one of a real time and near real time representation of the breast.

BRIEF DESCRIPTION OF THE DRAWINGS

For a further understanding of the objects and advantages of the present invention, reference should be made to the following detailed description, taken in conjunction with the accompanying figures, in which.

DESCRIPTION OF THE PREFERRED EMBODIMENTS

Figure 1:
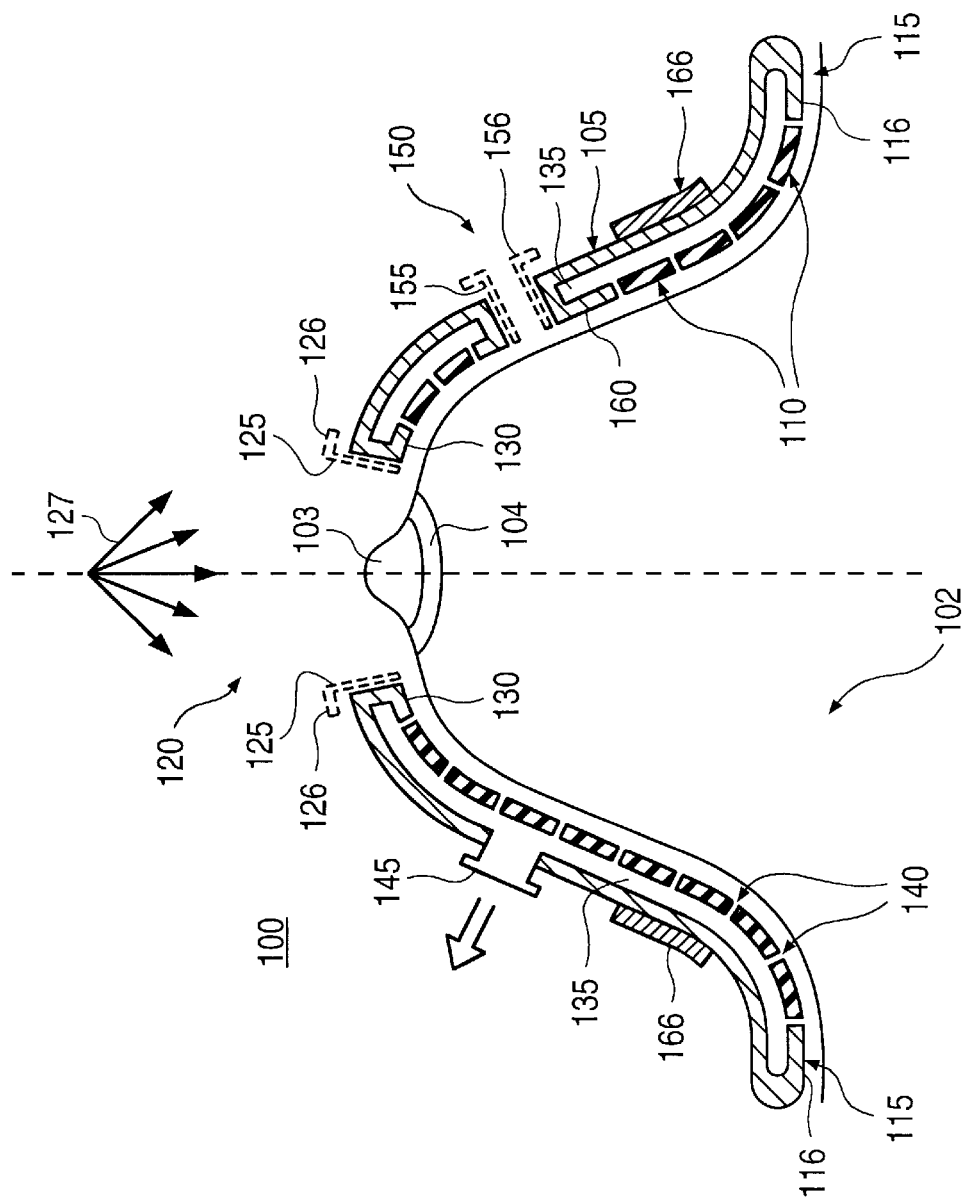
FIG. 1 is a cross section of an embodiment of the breast stabilizing device according to the present invention.

FIG. 1 is a cross-section of an embodiment of a breast stabilizing device 100 according to the present invention. The breast stabilizing device 100 is a generally cup- or generally hemispherical-shaped device configured to fit over the female breast 102 (not shown in cross-section). The breast stabilizing device 100 includes a substantially rigid outer member 105. The outer member 105 may be formed, for example, of a hard plastic material. The rigid outer member 105, according to an exemplary embodiment, is generally hemispherical in shape, and generally approximates the shape of the female breast in its natural, uncompressed state. The outer member 105 includes a curved base portion 115 that is configured to support the stabilizing device 100 against the patient's chest. As shown in FIG. 1, the curved portion 115 of the stabilizing device 100 curves to lay substantially flat against the patient's rib cage or other hard support. An inner member 110 is joined to the outer member 105. The inner member 110 is configured to conform closely to the shape of the breast 102. As the inner member 110 is preferably relatively softer and more flexible than the outer member 105, it is able to conform closely to the shape of the underlying breast 102. An opening 120 is disposed within the outer and inner members 105, 110, the opening 120 being aligned with the nipple/areolar complex 103/104 of the breast 102. A rigid rim 125 (shown in dashed lines) may surround the periphery of the opening 120 and may rise above the surface of the outer member 105. Alternatively, the rigid rim 125 may be omitted altogether. The rigid rim 125, if present, may be flush with the outer surface of the outer member 105. The opening 120 and the rim 125 are preferably centered on the nipple/areolar complex 103/104 and preferably expose at least a portion of the areola 104 surrounding the nipple 103. More preferably, the diameter of the opening 120 and the diameter of the rim 125 are such as to expose and to closely surround the circumference of the areola 104. If the rim 125 rises above the surface of the outer member 105, the height of the rim 125 above the surface of the outer member 105 and the inner diameter of the rim 125 should preferably allow free access by surgical needles and other instruments to the entire breast, as indicated by arrows 127. The rim 125 may includes a lip 126 or other similar structure to allow one or more instruments to be secured (e.g. clamped) thereto. The lip 126 may be integral to the rim 125, and the rim 125 may be integrally formed with the outer member 105. Alternatively, the rim 125 may be detachable, thereby allowing an assortment of such rims to be secured by, for example, a friction fit, to the breast stabilization device 100. In this manner, an assortment of rims 125 having different lip configurations or heights may be attached to the device 100 to allow a variety of medical instruments to be secured thereto. Preferably, the rim 125, when present and installed, is sealed to the inner member 110.

To insure a good seal between the breast 102 and the inner member 110 of the stabilizing device 100, a sealing edge 130 is disposed around the opening 120, the sealing edge being configured to seal the breast 102 to the opening 120. Preferably, the sealing edge 130 includes an adhesive layer disposed thereon to create a seal between the breast 102 and the opening 120. Similarly, the curved base portion 115 may also includes a sealing edge 116, the sealing edge 116 being configured to seal the breast stabilization device 100 against the patient's chest. In this manner, the breast stabilization device 100 may utilize the patient's own rib cage as a substantially rigid support platform. Preferably, the sealing edge 116 includes an adhesive layer disposed thereon to insure a proper seal between the patient's skin and the curved base portion 115.

According to another preferred embodiment, substantially the entire surface of the inner member 110 in contact with the patient's skin may also be coated with an adhesive layer, to insure that the stabilization device 110 is well secured to the breast 102. Prior to use, the physician may peel a protective film (not shown) from the inner surface of the inner member 110, thereby exposing the adhesive layer. Alternatively, the method of stabilizing an uncompressed breast according to the present invention may include a step of applying a preferably water soluble adhesive layer to the breast 102 prior to placing the breast stabilizing device 100 thereon. The adhesive layer disposed on the inner member 110 may be the same adhesive layer disposed on the sealing edge 116 of the curved base portion 115 and the sealing edge 130 of the opening 120.

As shown in FIG. 1, the outer member 105 and the inner member 110 are joined to one another. Although the outer member 105 may be substantially rigid to allow the physician to apply force thereon without collapsing the stabilization device 100, the inner member 110 is preferably relatively more flexible and softer than the outer member 105. This allows the inner member 105 to conform or to mold itself to the shape of the breast 102 as the stabilization device 100 is pressed thereon. To help insure that the relatively flexible inner member 110 molds itself to the breast 102 and to insure that the stabilizing device 100 seals itself against the breast 102, the inner member 110 and the outer member 105, according to a preferred embodiment, form a substantially gas-tight interstitial space 135 therebetween. In this embodiment, the inner member 110 includes a plurality of through holes or perforations 140 disposed therein. Alternatively, the outer member 105 and/or inner member 110 may include one or more channels disposed therein, the channel(s) being in fluid communication with the plurality of through holes 140. To insure a proper seal between the breast and/or the patient's chest and the device 100, the sealing edges 116, 130 preferably do not include through holes 140. The plurality of through holes 140 allow fluid (e.g. air) communication between the space enclosed by the stabilizing device 100 and the interstitial space 135. In this embodiment, the outer member 105 includes at least one suction port 145 that allows air to be evacuated from the interstitial space 135.

In use, the breast stabilizing device 102 is placed over the breast 102, and the opening 120 is aligned with the nipple/areolar complex 103/104. With the device 100 in place, the air present in the interstitial space 135 between the outer and inner members 105, 110 is drawn through the suction port 145, creating a partial vacuum within the interstitial space 135. The partial vacuum in the interstitial space 135 tends to draw any existing air that still exists between the breast 102 and the inner member 110 out through the through holes 140 and the suction port 145. In turn, the breast 102 is drawn towards and in intimate contact with the inner member 110, thereby sealing the stabilizing device 100 to the breast 102, leaving the nipple 103 and at least a portion of the areola 104 exposed through the opening 120. The opening 120 thereafter becomes the physician's primary access port to the breast 102 for invasive procedures. The suction through the suction port 145 may be accomplished by means of a syringe and plunger arrangement attached to the suction port 145, or through other conventional means known to those of skill in this art. As the inner member 110 is relatively more flexible and softer than the outer member 105, and as the air between the breast 102 and the inner member 110 is drawn out through the through holes 140 and the suction port 145, the inner member 110 molds itself to the breast 102, thereby securely adhering the stabilizing device 100 to the breast 102. When it is desired to release the patient's breast from the stabilizing device 100, low pressure air may be directed into the device through the suction port or ports 145. In this manner, the air forced through the port(s) 145 will gently break the seal created by the adhesive layer(s) and/or the previously applied suction, thereby allowing the device to be removed from the patient.

According to the present invention, suction may be employed to secure the stabilizing device 110 to the breast 102. Alternatively, adhesive layer(s) may be employed toward the same end. Alternatively still, suction and one or more adhesive layers may be employed in concert to secure the breast 102 to the stabilizing device 100. When suction is employed, whether alone or in combination with one or more adhesive layers applied to the inner member 110 or to the breast 102, the breast 102 may become somewhat expanded within the breast stabilization device 100. This slight expansion of the breast may actually aid in the visualization thereof by, for example, ultrasound techniques. By carefully matching the size and shape of the breast stabilizing device 100 to the patient's breast size and shape, a close fit may be achieved. This close fit will limit the degree of expansion (if any) of the breast as suction is applied through the suction port(s) 145 of the device 100.

As shown in FIG. 1, the breast stabilizing device 100 according to the present invention includes one or more imaging ports 150. The imaging port 150 includes an opening in both the outer and inner members 105, 110 to expose a portion of the side of the breast 102 therethrough. A sealing edge 160 on the inner member 110 surrounding the imaging port 150 seals the opening of the imaging port 150 against the breast 102. An adhesive layer (not shown) may be disposed on the sealing edge 160. The imaging port or ports 150 may include a rim 155 (shown in dashed lines) formed of a substantially rigid material, the rim 155 extending above the surface of the outer member 105. A lip 156 or other similar structure may be disposed on the rim 155. The lip 156 of the imaging port 150 allows one or more imaging instruments (not shown) to be secured (e.g. removably clamped) to the imaging port 150, without the physician having to manually hold the imaging device (not shown) in his or her hands. The rim 155 may be friction fitted to the imaging port 150 or may be secured thereto by other means.

According to the present invention, the physician may locate the target area within the breast 102 using an imaging device, such as an ultrasound probe. In that case, an acoustic coupling medium (such as a commonly available ultrasound gel) may be applied to the portion of the breast exposed through the imaging port or ports 150. For best results, the ultrasound device should be set at a frequency that balances the degree of penetration of the acoustic energy into the breast tissue with the desired or necessary resolution. Preferably, the ultrasonic probe should be set between a range selected from about 7.5 MHz to about 15 MHz. For example, the ultrasound probe may be set at a frequency of about 10 MHz.

Once the site of interest is located with the probe, the probe may be attached or clipped to the imaging port 150. In this manner, the surgeon's hands are not only freed from the need to manually stabilize the breast, but are also freed from having to hold the ultrasound probe while carrying out the biopsy or excisional procedure. Therefore, the physician may concentrate his or her attention on the task at hand, namely the accurate targeting and sampling and/or excising of the lesion within the breast 102. Moreover, utilizing the breast stabilizing device 100 according to the present invention, the physician need no longer insert the biopsy needle parallel to the patient's chest wall, as previously necessary using conventional sonographically guided techniques. Indeed, as the breast 102 is well stabilized within the breast stabilizing device 100 and correctly imaged by the imaging device(s) attached to the imaging port(s) 150, there is no longer any need to insert the needle parallel to the chest wall or to suffer the disadvantages alluded to above that are concomitant with introducing the needle in a direction that is substantially parallel to the lactiferous duct structures within the breast 102. Indeed, the primary access port of the breast stabilizing device 100 is the opening 120 that is aligned with the nipple 103. By providing a procedure-facilitating platform that allows free accessing to a stabilized and uncompressed breast 102 in a direction that is substantially aligned with the lactiferous ducts, superior results may be obtained with substantially decreased trauma to the patient.

The stabilizing device 100 may include more than one imaging port 150. In fact, the breast stabilizing device 100 is ideally suited to carry out any type of ultrasonic imaging, such as, for example, true 3-D real time (or near real time) ultrasonic imaging. Indeed, by providing two or more imaging ports 150 on the breast stabilizing device 100 according to the present invention separated by, for example, about 15 degrees or more, a three dimensional representation of the inner breast structure may be rendered on a computer display terminal for the physician's reference during the procedure itself. As the tip of the biopsy needle or other interventional tool may be opaque to ultrasounds, the surgeon may guide her instrument within the breast while consulting a real time or near real time digital representation of the breast 102. In this manner, a feedback loop between the surgeon and the digital representation of the uncompressed and stabilized breast 102 is now possible. The surgeon may then confirm, for example, that the lesion site has indeed been reached or that the entire lesion has been excised by consulting the digital representation of the breast 102 before the procedure is over.

The imaging port or ports 150 may be generally circular in shape, or may have a shape that accommodates the particular imaging device to be used therewith. For example, the imaging port or ports 150 may have a shape resembling arcs or curved channels, thereby allowing the physician to reposition and re-clamp the imaging device thereto if needed during the procedure. Care should be taken not to unduly weaken the structure of the stabilizing device 100 by including too many ports and/or other openings therein.

The breast stabilizing device 100 may include securing means 165 to secure the device 100 to a substantially immobile structure such as, for example, a procedure table or chair. In the embodiment of the stabilizing device illustrated in FIG. 1, the securing means 165 includes a substantially rigid band 166 that girdles the device 100. Such rigid band 166 may be removably secured to the outer member 105 by means of integral retaining flanges 167 that prevent or restrict movement of the band 166. The band 166 may include or be attached to a shaft (not shown) that is, in turn, attached to a substantially immobile structure, such as the procedure table or chair. Such a procedure table or chair would preferably position the patient so that her breast hangs down somewhat. In this manner, the breast stabilizing device 100 may be fitted to the patient's breast with ease, gravity helping to bring the breast 102 into the device 100. Alternatively, the patient may be asked to lean forward somewhat, to accomplish similar results. Other means of securing the breast stabilizing device may be employed without, however, departing from the scope of the present invention. Alternatively, the securing means 165 may be omitted in its entirety. Preferably, the securing means should be adjustable and removable, to permit stabilizing devices 100 of various sizes and shapes to be attachable thereto.

The device 100 is preferably sterile, and may either be disposable or made from materials that are suitable for multiple uses and that may be autoclaved. Disposable stabilizing devices, however, minimize the risk of transmitting harmful viruses, such as the HIV or hepatitis B virus, or other diseases communicable by bodily fluids.

In another embodiment of the present invention, the stabilizing device 100 may not only include a generally breast-shaped portion, but may also include a hard shell covering the patient's entire thorax. Such a hard shell would further stabilize the device 100, and further inhibit the patient's movements. Such a hard shell may further extend at least partially over the patient's back and/or may be securable to the patient or to some other structure by means of VELCRO® hook and loop fasteners or other arrangements, such as buckles. The hard shell may be integral with or distinct from the stabilizing device 100.

In a further embodiment, the patient's other breast may also be secured to a device identical or similar to that shown at 100 in FIG. 1. The two such devices may then be interconnected, such as by their respective securing means 165, and the assembly secured to the patient with adjustable straps, like a bra. In this manner, the forces applied to the breasts are symmetrical and the patient's movements may be further inhibited. The breast stabilization device may be reusable or may be disposable.

While the foregoing detailed description has described several embodiments of this invention, it is to be understood that the above description is illustrative only and not limiting of the disclosed invention. For example, the number and shape of the imaging, access and suction ports may differ from that illustrated and described herein, without, however, departing from the spirit and scope of the present invention. A number of other modifications will no doubt occur to persons of skill in this art. All such modifications, however, should be deemed to fall within the scope of the present invention. Thus, the invention is to be limited only by the claims as set forth below.

What is claimed is:

1. A breast stabilization device for imaging and invasive procedures, comprising:
   a substantially rigid outer member;
   an inner member joined to the outer member, the inner member being configured to generally conform to a shape of a female breast;
   an opening disposed through the outer and inner members, the opening being adapted to align with a nipple/areola complex of the breast, and
   at least one imaging port disposed within a side surface of at least the outer member.

2. The device of claim 1, further comprising a rigid rim surrounding a periphery of the opening and rising above a surface of the outer member.

3. The device of claim 2, wherein the rigid rim includes a lip configured to allow at least one instrument to be secured thereto.

4. The device of claim 2, wherein the rim is integral to the outer member.

5. The device of claim 1, wherein the opening is configured to expose at least a portion of an areola surrounding the nipple.

6. The device of claim 1, wherein at least the inner member comprises a curved base portion configured to support the device against a patient's chest.

7. The device of claim 6, wherein the base portion comprises a second sealing edge, the second sealing edge being configured to seal the device to the patient's chest.

8. The device of claim 7, wherein the second sealing edge includes a second adhesive layer disposed thereon.

9. The device of claim 1, further comprising a first sealing edge around the opening, the first sealing edge being configured to seal the breast to the opening.

10. The device of claim 9, wherein the first sealing edge includes a first adhesive layer disposed thereon.

11. The device of claim 1, further comprising an imaging port rim adapted to fit within the imaging port, the imaging port rim allowing at least one imaging instrument to be secured thereto.

12. The device of claim 11, further comprising an imaging port sealing edge surrounding each of the at least one imaging port, each imaging port sealing edge being configured to seal the breast around its corresponding imaging port.

13. The device of claim 1, wherein the inner member includes an inner member adhesive layer disposed on a surface thereof facing the breast.

14. The device of claim 1, wherein the inner member includes a plurality of through holes disposed therein.

15. The device of claim 14, wherein the inner member and the outer member are configured to form a substantially gas-tight interstitial space therebetween and wherein the device further comprises at least one suction port disposed in the outer member.

16. The device of claim 1, further comprising securing means attached to the outer member, the being adapted to secure means securing the breast stabilization device to at least one of a table and a chair.

17. The device of claim 16, wherein the securing means includes a substantially rigid band girdling the breast stabilizing device.

18. The device of claim 1, wherein the inner member is relatively more flexible than the outer member.

19. A procedure facilitating platform for a breast, comprising:
   a generally breast shaped member configured to cover at least a portion of the breast;
   suction means for drawing the breast shaped member in close contact with the breast;
   an access port disposed in the generally breast shaped member, and
   at least one imaging port, the at least one imaging port being disposed in a side of the generally breast shaped member.

20. The procedure facilitating platform of claim 19, wherein the first access port is adapted to be centered on the nipple/areolar complex of the breast when the platform is in use.

21. A method of imaging a breast, comprising the steps of:
   placing a generally breast shaped member on the breast, the breast shaped member having a first imaging port therein;
   expanding the breast to come into intimate contact with the breast shaped member; and
   imaging the breast through the first imaging port.

22. The method of claim 21, wherein the expanding step is carried out by creating a partial vacuum between the breast and the breast shaped member.

23. The method of claim 21, wherein the first imaging port exposes a portion of the breast therethrough and the imaging step includes a step of directing ultrasonic energy into the breast through the first imaging port.

24. The method of claim 23, further comprising the step of applying an ultrasound coupling medium within the first imaging port prior to the directing step.

25. The method of claim 21, wherein the breast shaped member includes a second imaging port and wherein the imaging step images the breast through the first and the second imaging ports.

26. The method of claim 25, wherein the breast is imaged through the first and second imaging ports simultaneously.

27. The method of claim 26, further including the steps of:

processing imaging data obtained from each of the first and second imaging ports in a data processing and display device; and displaying the processed image data as one of a real time and near real time representation of the breast.

28. The method of claim 21, wherein the imaging step generates imaging data and wherein the imaging data is transmitted to at least one data processing and display device.

29. A breast stabilization device for imaging and invasive procedures, comprising:

a substantially rigid outer member;

an inner member joined to the outer member, the inner member being configured to generally conform to a shape of a female breast and comprising a curved base portion configured to support the device against a patient's chest, the curved base portion comprising a sealing edge that is configured to seal the device to the patient's chest, and an opening disposed through the outer and inner members, the opening being adapted to align with a nipple/areola complex of the breast.

30. A breast stabilization device for imaging and invasive procedures, comprising:

a substantially rigid outer member;

an inner member joined to the outer member, the inner member being configured to generally conform to a shape of a female breast and including a plurality of through holes disposed therein, the inner member and the outer member being adapted to form a substantially gas-tight interstitial space therebetween when the device is applied to the breast;

an opening disposed through the outer and inner members, the opening being adapted to align with a nipple/areola complex of the breast, and at least one suction port disposed in the outer member.

31. A breast stabilization device for imaging and invasive procedures, comprising:

a substantially rigid outer member;

an inner member joined to the outer member, the inner member being configured to generally conform to a shape of a female breast;

an opening disposed through the outer and inner members, the opening being adapted to align with a nipple/areola complex of the breast, and securing means attached to the outer member, the securing means being adapted to secure the breast stabilization device to at least one of a table and a chair.

32. The device of claim 31, wherein the securing means includes a substantially rigid band girdling the breast stabilizing device.

33. A method of stabilizing an uncompressed breast, comprising the steps of:

placing a generally breast-shaped member over the uncompressed breast, the breast-shaped member including an opening aligned with and exposing at least a portion of a nipple/areolar complex of the breast; and sealing the breast within the shaped—shaped member by means of at least one of an adhesive and a vacuum-induced force that draws the breast thereto.

34. The method of claim 33, further comprising the step of:

securing the cup-shaped member to a stable positional reference structure.

* * * * *